(12) United States Patent
Chornet et al.

(10) Patent No.: US 8,105,480 B2
(45) Date of Patent: Jan. 31, 2012

(54) PROCESS FOR TREATING HEAVY OILS

(75) Inventors: Michel Chornet, Sherbrooke (CA); Esteban Chornet, Sherbrooke (CA)

(73) Assignee: Fractal Systems, Inc., Sherbrooke, Quebec (CA)

( * ) Notice: Subject to any disclaimer, the term of this patent is extended or adjusted under 35 U.S.C. 154(b) by 259 days.

(21) Appl. No.: 11/983,842

(22) Filed: Nov. 13, 2007

(65) Prior Publication Data

US 2008/0217211 A1 Sep. 11, 2008

Related U.S. Application Data

(60) Provisional application No. 60/905,171, filed on Mar. 6, 2007.

(51) Int. Cl.
*C10G 9/34* (2006.01)
*C10G 9/00* (2006.01)
(52) U.S. Cl. .................................... 208/125; 208/106
(58) Field of Classification Search .................. 208/106, 208/125
See application file for complete search history.

(56) References Cited

U.S. PATENT DOCUMENTS

| 4,401,606 A | 8/1983 | Matsuoka |
| 4,915,819 A * | 4/1990 | Chirinos et al. ............. 208/309 |
| 5,096,566 A | 3/1992 | Dawson et al. |
| 5,810,052 A | 9/1998 | Kozyuk |
| 5,969,207 A | 10/1999 | Kozyuk |
| 6,035,897 A | 3/2000 | Kozyuk |
| 2003/0019791 A1 * | 1/2003 | Austin ......................... 208/106 |
| 2006/0231462 A1 | 10/2006 | Johnson |

FOREIGN PATENT DOCUMENTS

WO WO02/102746 A1 12/2002
WO WO2006/067636 A2 6/2006

* cited by examiner

*Primary Examiner* — Walter D Griffin
*Assistant Examiner* — Renee E Robinson
(74) *Attorney, Agent, or Firm* — Elliot M. Olstein; Raymond J. Lillie

(57) ABSTRACT

A process for treating a heavy oil which comprises subjecting a heavy oil to cavitation to reduce the viscosity of the heavy oil. The treated heavy oil, which has a reduced viscosity and specific gravity, thus is more pumpable and transportable, which facilitates further processing. The treated heavy oil also can be fractionated with less severity than untreated heavy oil.

55 Claims, 4 Drawing Sheets

PROCESS FOR TREATING HEAVY OILS

This application claims priority based on provisional application Ser. No. 60/905,171, filed Mar. 6, 2007, the contents of which are incorporated by reference in their entirety.

This invention relates to a process for treating heavy oils. More particularly, this invention relates to a process for treating heavy oils by destructuring such heavy oils through molecular rearrangement, thereby reducing the viscosity of such heavy oils. Such treating is effected by subjecting a heavy oil to cavitation. The treated heavy oil has a reduced viscosity due to molecular rearrangement, and its further processing or upgrading may be effected under conditions of lower severity than untreated heavy oil.

The term "heavy oil", as used herein, includes oils which are classified by the American Petroleum Institute (API), as heavy oils or extra heavy oils. In general, a heavy hydrocarbon oil has an API gravity between 22.3° (density of 920 kg/m$^3$ or 0.920 g/cm$^3$) and 10.0° (density of 1,000 kg/m$^3$ or 1 g/cm$^3$). An extra heavy oil in general has an API gravity of less than 10.0° (density greater than 1,000 kg/m$^3$ or greater than 1 g/cm$^3$). For example, heavy oils may be extracted from oil sands, atmospheric tar bottoms products, vacuum tar bottoms products, shale oils, coal-derived liquids, crude oil residues, and topped crude oils.

Such heavy oils, however, are highly viscous and difficult to pump through pipelines, and require high severity techniques for upgrading.

Heavy oils in general have macro and micro structural properties as well as having specific chemical constitutive molecules. The chemical constitutive molecules belong to two generic categories, maltenes and asphaltenes. Maltenes are soluble in 40 volumes of pentane, while asphaltenes are soluble in toluene but insoluble in pentane. Also present in the heavy oils are metals, particularly nickel and vanadium. The metals are associated mainly with the asphaltenes. The spatial organization of maltenes and asphaltenes results in the macro and micro structural properties, with the molecular organization causing the high viscosities, which pose a problem in transporting such oils, and in separating the asphaltenes from the maltenes.

More particularly, the asphaltenes are formed by a core of polynuclear aromatic molecules grouped in layers, to which alkyl chains are attached. The core is surrounded by and immersed in the maltene material. The maltene material includes free saturates (some of them cyclic), mono- and diaromatics and resins which are believed to be associated closely with the asphaltenes. This organization is considered to be the microstructure and the core of the asphaltenes can be considered as possessing microcrystalline arrangements. The microstructural organization forms aggregates in which several microcrystalline arrangements form a micellar structure known as a macrostructure. The micellar structure or macrostructure has strong associative and cohesive forces between the aggregates, which accounts for the high viscosity of the heavy oil.

U.S. Pat. No. 5,096,566 discloses a method of reducing the viscosity of a heavy oil by heating a heavy hydrocarbon oil to a temperature of 350°-450° C., and heating a gas, such as hydrogen or nitrogen, to a temperature of 400-900° C. The heavy oil and the heated gas then are mixed in a mixer, and the mixture of heavy oil and gas in the mixer is subjected to a pressure of from 700 to 2,000 psi. The mixture then is passed through a small nozzle or orifice such that a pressure drop of from 500 to 1,500 psi occurs across the nozzle or orifice, and the heavy oil and gas mixture is ejected from the nozzle or orifice, thereby providing an oil having a reduced viscosity. When the heavy oil is mixed with the hydrogen, mild hydrocracking of the heavy oil also occurs. This oil then may be processed further, such as in a reaction zone, for example.

In accordance with an aspect of the present invention, there is provided a process for treating a heavy oil. The process comprises subjecting a liquid comprising a heavy oil to cavitation in order to reduce the viscosity of the heavy oil.

In a non-limiting embodiment, the heavy oil is treated in the absence of hydrogen.

The term "liquid", as used herein, means a liquid at standard temperature and pressure.

The term, "standard temperature and pressure," as used herein, means 1 atmosphere pressure and 15° C.

As is known in the art, cavitation means the formation, growth, and collapse or implosion of gas or vapor filled bubbles in liquids. Cavitation requires the presence of small and transient microcavities or microbubbles of vapor or gas. The microcavities or microbubbles grow, and then implode or collapse. The implosion, or sudden compression and collapse of the microcavities or microbubbles raises the temperature of the interface between the microcavities or microbubbles and the heavy oil for very short time intervals, i.e., microseconds. Such temperature increases facilitate free radical formation and chemical reaction.

Thus, during cavitation, a portion of the liquid comprising the heavy oil is in the form of a gas which is dispersed as bubbles in the liquid portion.

Such cavitation may be effected by means known to those skilled in the art, such as, for example, by hydrodynamic cavitation, or ultrasonic cavitation. It is to be understood, however, that the scope of the present invention is not to be limited to any specific method of effecting cavitation.

In a non-limiting embodiment, the liquid comprising the heavy oil is subjected to hydrodynamic cavitation. In hydrodynamic cavitation, the liquid comprising the heavy oil, a portion of which is in the form of a gas dispersed in the liquid, is passed through a restriction or cavitation zone, such as, for example, a capillary or nozzle, to increase the velocity of the mixture. The gaseous portion may be present prior to passing the liquid comprising the heavy oil through the cavitation zone and/or such gaseous portion may be produced as a result of the pressure drop that results from passing the liquid comprising the heavy oil through the cavitation zone.

In general, one can determine whether hydrodynamic cavitation has occurred by determining the cavitation number for the heavy oil, which is passed through the cavitation zone. The cavitation number may be determined in metric units according to the following equation:

$$\sigma c = \frac{2(P - Pv)}{\rho V^2}$$

wherein $\sigma c$ is the cavitation number, $P$ is the local static pressure of the heavy oil, $Pv$ is the vapor pressure of the heavy oil, $\rho$ is the density of the heavy oil, and $V$ is the velocity of the heavy oil.

In general, depending upon the exact parameters employed, the cavitation number, $\sigma c$, does not exceed 1.5. It is to be understood, however, that, within the scope of the present invention, there may be cavitation in certain instances when the cavitation number is greater than or equal to 1.5.

In a non-limiting embodiment, the liquid comprising the heavy oil is passed through the cavitation zone, which may be in the form of a capillary or nozzle or other type of restriction, at a velocity of from about 100 m/sec to about 300 m/sec, and as the liquid comprising the heavy oil passes through the cavitation zone such as a capillary or nozzle, the liquid comprising the heavy oil is subjected to a pressure drop of from about 150 psig to about 5,000 psig. In the cavitation zone, the heavy oil is subjected to cavitation. As known in the art, cavitation is produced by microbubbles of gas dispersed in the heavy oil. Such microbubbles expand and then implode or collapse. The implosion or collapse of the microbubbles raises the temperature at the interface of the microbubbles and heavy oil to very high levels, for example, from about 1,000° C. to about 2,000° C., for a period of microseconds, which facilitates free radical formation and chemical reactions.

In a non-limiting embodiment, the liquid comprising the heavy oil is passed through the cavitation zone at a velocity of from about 150 m/sec to about 300 m/sec. In another embodiment, the liquid comprising the heavy oil is passed through the cavitation zone at a velocity of from about 200 m/sec to about 300 m/sec.

In a non-limiting embodiment, the liquid comprising the heavy oil is subjected to a pressure drop in the cavitation zone of from about 400 psig to about 4,000 psig. In another non-limiting embodiment, the liquid comprising the heavy oil is subjected to a pressure drop in the cavitation zone of from about 400 psig to about 2,000 psig. In another embodiment, the liquid comprising the heavy oil is subjected to a pressure drop in the cavitation zone of from about 400 psig to about 1,500 psig. In yet another embodiment, the liquid comprising the heavy oil is subjected to a pressure drop in the cavitation zone of from about 1,000 psig to about 1,500 psig.

In a non-limiting embodiment, the ratio of the length of the cavitation zone to the width of the cavitation zone is from about 10 to about 125. In another non-limiting embodiment, the ratio of the length of the cavitation zone to the width of the cavitation zone is from about 50 to about 125.

In a non-limiting embodiment, the heavy oil is heated and then the heavy oil is subjected to conditions which produce cavitation as hereinabove described.

In a non-limiting embodiment, the heavy oil is heated to a temperature of from about 75° C. to about 450° C. In another embodiment, the heavy oil is heated to a temperature of from about 150° C. to about 450° C. In another embodiment, the heavy oil is heated to a temperature of from about 200° C. to about 450° C. In yet another embodiment, the heavy oil is heated to a temperature of from about 200° C. to about 400° C. In still another embodiment, the heavy oil is heated to a temperature of from about 300° C. to about 400° C.

Although the scope of the present invention is not intended to be limited thereby, in general the heavy oil to be treated may be those oils referred to by the American Petroleum Institute (API) as heavy oils and extra heavy oils. As noted hereinabove, a heavy oil has an API gravity of between 22.3° (density of 920 kg/m$^3$ or 0.920 g/cm$^3$) and 10.0° (density of 1,000 kg/m$^3$ or 1 g/cm$^3$). An extra heavy oil has an API gravity of less than 10.0° (density greater than 1,000 kg/m$^3$ or greater than 1 g/cm$^3$). Examples of such heavy oils include, but are not limited to, bitumen, heavy oils extracted from below the ground surface by steam assisted gravity drainage, or SAGD, and other methods, bottoms products from atmospheric or vacuum distillation of bitumen or heavy oil, shale oils, coal-derived liquids, crude oil residues, and topped crude oils.

In another non-limiting embodiment, a portion of the heavy oil when heated may or may not be vaporized.

In a non-limiting embodiment, the portion of the heavy oil which is vaporized does not exceed 35 vol. % of the volume of the heavy oil. In another non-limiting embodiment, the portion of the heavy oil which is vaporized does not exceed 15 vol. % of the volume of the heavy oil.

In a non-limiting embodiment, the liquid further comprises an organic material, that is not a heavy oil and is a liquid at standard temperature and pressure. Thus, in a non-limiting embodiment, there is provided a process for treating a heavy oil which comprises subjecting a heavy oil in combination with an organic material to cavitation in order to reduce the viscosity of the heavy oil.

The mixture of the heavy oil and organic material may be subjected to cavitation as hereinabove described. For example, the mixture of the heavy oil and organic material may be passed through the cavitation zone under the velocity and pressure drop conditions mentioned hereinabove.

In addition, when the mixture of heavy oil and organic material is subjected to hydrodynamic cavitation, a portion of the mixture of heavy oil and organic material is in the form of a gas dispersed in the liquid. The gaseous portion may be (i) a portion or all of the organic material, or (ii) both a portion or all of the organic material and a portion of the heavy oil, or (iii) only a portion of the heavy oil. Preferably, the gas includes the organic material and may or may not include a portion of the heavy oil.

In a non-limiting embodiment, each of the heavy oil and organic material is heated, the heavy oil and the organic material are mixed, and then the mixture of heavy oil and organic material is subjected to conditions which produce cavitation as hereinabove described.

In a non-limiting embodiment, subsequent to the heating of the heavy oil and organic material, the heavy oil and organic material are mixed in a mixing zone, and then subjected to cavitation in the cavitation zone.

In another non-limiting embodiment, a portion of the heavy oil when heated, prior to being mixed with the organic material in the mixing zone, may or may not be vaporized. If a portion of the heavy oil is vaporized, such portion, in a non-limiting embodiment, does not exceed the amounts hereinabove described.

In another non-limiting embodiment, when heated (prior to being mixed with the heavy oil in the mixing zone), all or a portion of the organic material is vaporized.

In another non-limiting embodiment, the organic material, when heated (prior to being mixed with the heavy oil in the mixing zone), remains a liquid. In yet another non-limiting embodiment, when such liquid organic material is passed through the cavitation zone, all or a portion of such liquid organic material is vaporized.

In another non-limiting embodiment, the organic material has been subjected to a temperature above the critical temperature and a pressure above the critical pressure and thus becomes a supercritical fluid, which has properties of a liquid and a gas. The result is that the organic material has the ability to interact or associate with components of the heavy oil which are similar to those as when the organic material exists as a liquid, but it has a higher diffusivity, lower viscosity, and lower surface tension than such material in the liquid phase. It is to be understood that the scope of the present invention is not to be limited to such an embodiment.

Thus, in a non-limiting embodiment, at least a portion of the mixture of heavy oil and organic material is a liquid. In one embodiment, the amount of the mixture which is a liquid is an amount sufficient to form a continuous liquid phase which is subjected to cavitation as hereinabove described. In a non-limiting embodiment, liquid is present in an amount of at least 40 vol. % of the total volume of the mixture of heavy oil and organic material. In another embodiment, liquid is present in an amount of at least 60 vol. % of the total volume of heavy oil and organic material.

In a non-limiting embodiment, the organic material induces selective molecular interactions that change the molecular environment of the asphaltenes, such as, for example, through Van der Waals forces, dispersion forces, and dipole-dipole interactions, thereby inducing changes in the micellar structure and facilitating the subsequent separation of asphaltenes from the heavy oil. In one embodiment, the organic material interacts or associates with one or more of the components of the heavy oil, but does not interact with the asphaltenes. In another embodiment, the organic material interacts with or associates with the asphaltenes.

As noted hereinabove, the organic material is a material that is not a heavy oil and is a liquid at standard temperature and pressure.

In yet another non-limiting embodiment, the organic material is an organic solvent.

Examples of organic materials which may be employed within the scope of the present invention include, but are not limited to, pentane, liquefied petroleum gases (LPGs), alcohols, such as methanol and ethanol, for example, and ethers, such as, for example, alkyl ethers such as dimethyl ether and diethyl ether, and mixtures thereof.

In a non-limiting embodiment, the organic material is heated to a temperature of from about 75° C. to about 800° C. In another non-limiting embodiment, the organic material is heated to a temperature of from about 150° C. to about 800° C. In another embodiment, the organic material is heated to a temperature of from about 300° C. to about 800° C. In yet another embodiment, the organic material is heated to a temperature of from about 300° C. to about 600° C. In still another embodiment, the organic material is heated to a temperature of from about 300° C. to about 400° C.

In a non-limiting embodiment, the organic material is present in the mixture of heavy oil and organic material in an amount of from about 5 vol. % to about 25 vol. % of the volume of heavy oil. In another embodiment, the organic material is present in an amount of from about 5 vol. % to about 10 vol. % of the volume of the heavy oil.

In another non-limiting embodiment, the heated heavy oil enters a mixing zone, or mixing chamber as a result of pumping the heated oil through a first conduit, and the heated organic material enters the mixing chamber as a result of pumping the heated organic material through a second conduit. In one embodiment, the first conduit, through which the heavy oil enters the mixing zone, terminates at an atomization nozzle, whereby the heavy oil is atomized as it enters the mixing zone or mixing chamber. In one embodiment, the atomization nozzle has a shape which facilitates the atomization of the heavy oil, such as, for example, a conical shape. Thus, the heavy oil enters the mixing zone or mixing chamber as a spray or mist of liquid droplets. The presence of the heavy oil in the form of liquid droplets increases the surface area of the heavy oil and provides for better mixing of the heavy oil and the organic material.

In one non-limiting embodiment, the organic material enters the mixing zone in a direction of flow which in effect is tangential to the direction of flow of the heavy oil through the mixing zone. More particularly, the organic material enters the mixing zone through a conduit as hereinabove described such that when the organic material enters the mixing zone, the organic material moves along the wall of the mixing zone in a circular or vortexing motion. The heavy oil, which enters the mixing zone through an atomization nozzle as hereinabove described contacts and becomes admixed with the vortexing organic material. Such vortexing of the heavy oil and organic material facilitates optimal mixing of the organic material and the heavy oil. The vortexed mixture of the heavy oil and organic material then is passed to and subjected to cavitation in the cavitation zone. It is to be understood, however, that the scope of the present invention is not to be limited by such an embodiment.

In another non-limiting embodiment, the heavy oil and the organic material are mixed in a conduit, and then the mixture of heavy oil and the organic material are subjected to further mixing in a static mixer. In the static mixer, the stream including the mixture of heavy oil and organic material is divided, and the divided streams are forced to opposite outside walls, thereby causing a single direction mixing vortex axial to the center line of the static mixer. The mixing vortex then is sheared, and a division of the stream of heavy oil and organic material reoccurs with the opposite directional rotation.

In a non-limiting embodiment, the mixing zone or mixing chamber is configured such that the mixing zone or mixing chamber facilitates the mixing of the heavy oil and organic material to provide an essentially uniform mixture of the heavy oil and organic material. In one non-limiting embodiment, the mixing zone or mixing chamber has a cylindrical configuration. In one non-limiting embodiment, the cylinder has a length to diameter ratio of from about 1 to about 36. In another non-limiting embodiment, the cylinder has a length to diameter ratio of about 4. In yet another non-limiting embodiment, the cylinder has a length to diameter ratio of about 2. It is to be understood, however, that the scope of the present invention is not to be limited to any specific configuration of the mixing zone or mixing chamber.

The organic material and heavy oil, in a non-limiting embodiment, are mixed in the mixing zone or mixing chamber for a period of time sufficient to provide an essentially uniform mixture of the heavy oil and organic material, yet such mixture of heavy oil and organic material is not retained in the mixing zone for a prolonged period of time such that undesired thermal cracking occurs.

In a non-limiting embodiment, the organic material and heavy oil are mixed in the mixing zone for a period of time which does not exceed 10 seconds. In another embodiment, the organic material and heavy oil are mixed in the mixing zone for a period of time of from about 1 second to about 10 seconds.

The organic material induces selective molecular interactions that contribute in changing the molecular environment of the asphaltenes through solvation.

After the heavy oil and organic material are mixed in the mixing zone or mixing chamber, the mixture of heavy oil and organic material exits the mixing zone or mixing chamber, and enters the cavitation zone, in which the heavy oil is subjected to cavitation as hereinabove described.

In a non-limiting embodiment, when the heavy oil is subjected to hydrodynamic cavitation, the heavy oil is passed from the mixing zone to the cavitation zone, which is a restriction such as a capillary or nozzle, in which cavitation occurs. The width of the cavitation zone is less than that of the mixing zone. In a non-limiting embodiment, the ratio of the width of the cavitation zone to the width of the mixing zone is from about 1/230 to about 1/75.

Thus, the mixture of heavy oil and organic material is passed from the mixing zone through the restriction or cavitation zone to increase the velocity of the mixture, and whereby the mixture is subjected to a pressure drop. As a result, in the cavitation zone microbubbles are dispersed in the liquid portion of the mixture. Such microbubbles initially expand, and then they implode or collapse, thus effecting cavitation of the heavy oil.

The resulting heavy oil product which is released from the cavitation zone is a destructured heavy oil that, upon cooling, has different micellar arrangements (reflected by a lower viscosity) than those of the heavy oil prior to being mixed with the organic material and subjected to cavitation as described hereinabove. Although the scope of the present invention is not intended to be limited to any theoretical reasoning, the cavitation of the heavy oil, which is the result of microbubbles in the heavy oil, raises the temperature of the interface of the microbubbles, thereby facilitating free radical formation and chemical reaction. Also the organic material induces selective molecular interaction that change the molecular environment of the asphaltenes. In addition, if the temperature is raised during the treatment, some incipient cracking may occur, which results in the release of saturated hydrocarbon alkyl chains present in the initial asphaltenes which thus will become easier to separate from the oil. The present invention thus enables the destructuring of a heavy oil by adding a small amount of organic material and by subjecting the heavy oil to cavitation, as opposed to supplying excessive amounts of compressed gas. The gas is replaced by a small amount of an organic material which is capable of being at least partially vaporized.

After the mixture of heavy oil and organic material has been subjected to cavitation in the cavitation zone as hereinabove described, the mixture is released from the cavitation zone and is cooled to a desired temperature, such as, for example, in a non-limiting embodiment, by passing the mixture to an expansion zone or chamber or a flash chamber and the gas is separated partially or totally from the liquid. Although the components and the "distillation curve" of the resulting destructured heavy oil approximate those of the heavy oil prior to destructuring, the destructured heavy oil produced in accordance with the present invention has a reduced viscosity, a reduced specific gravity, and can be fractionated more easily than untreated heavy oil, i.e., the asphaltenes may be separated from the maltenes more easily, such as by precipitation, absorption, or microfiltration.

The present invention thus provides a destructured heavy oil that is more pumpable or transportable, and thus can be transported more easily for further processing, and can be fractionated with less severity than in its original state. For example, the destructured heavy oil may be subjected to deasphalting, whereby the asphaltenes are separated from the heavy oil, and to provide an upgraded de-asphalted oil which may be subjected to further refining or processing. Alternatively, the heavy oil may be distilled into various fractions.

BRIEF DESCRIPTION OF THE DRAWINGS

The invention now will be described with respect to the drawings, wherein.

Figure 1:
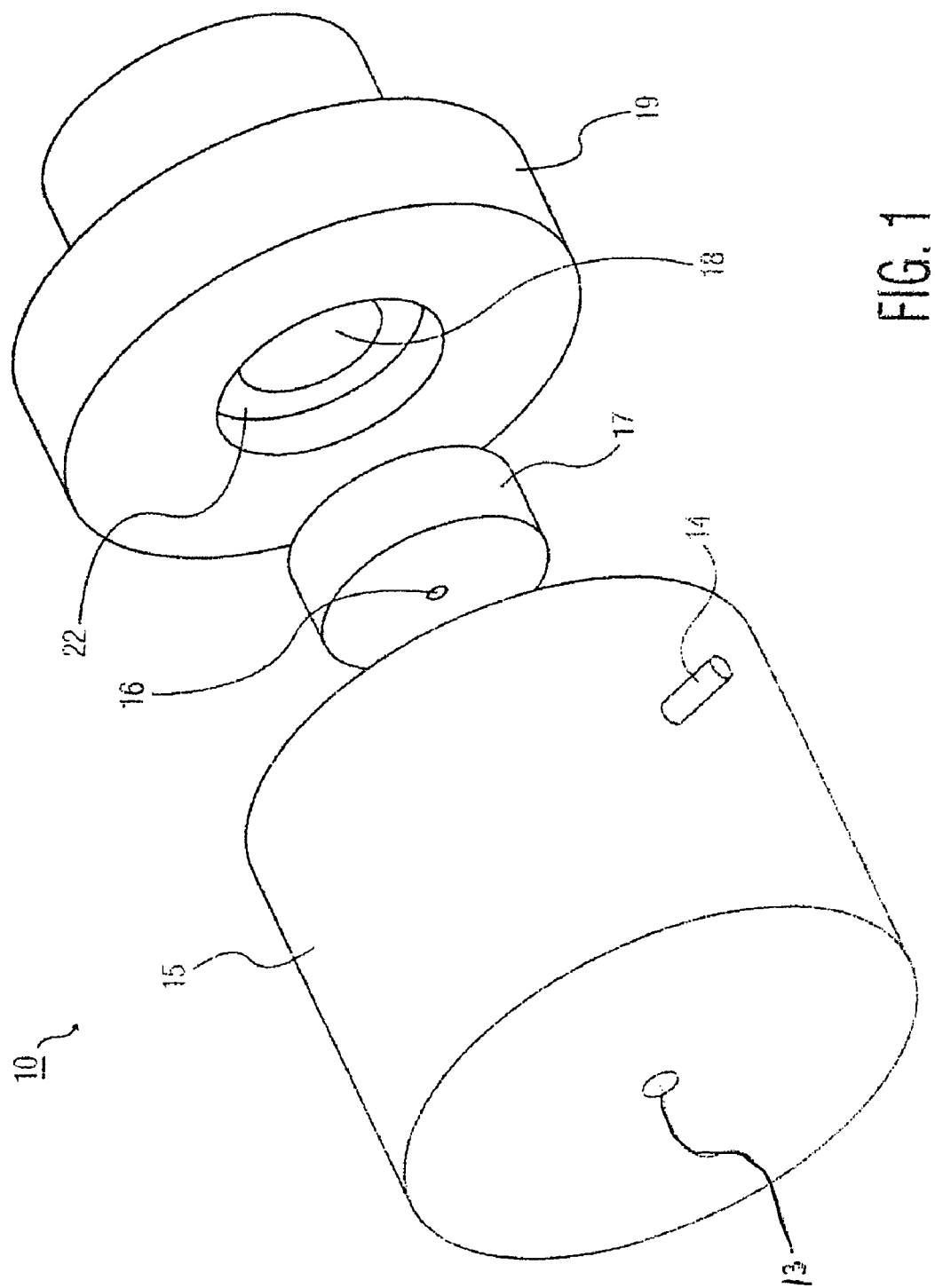
FIG. 1 is an exploded view of an embodiment of an apparatus for effecting the destructuring of a heavy oil in accordance with the present invention.
Figure 2:
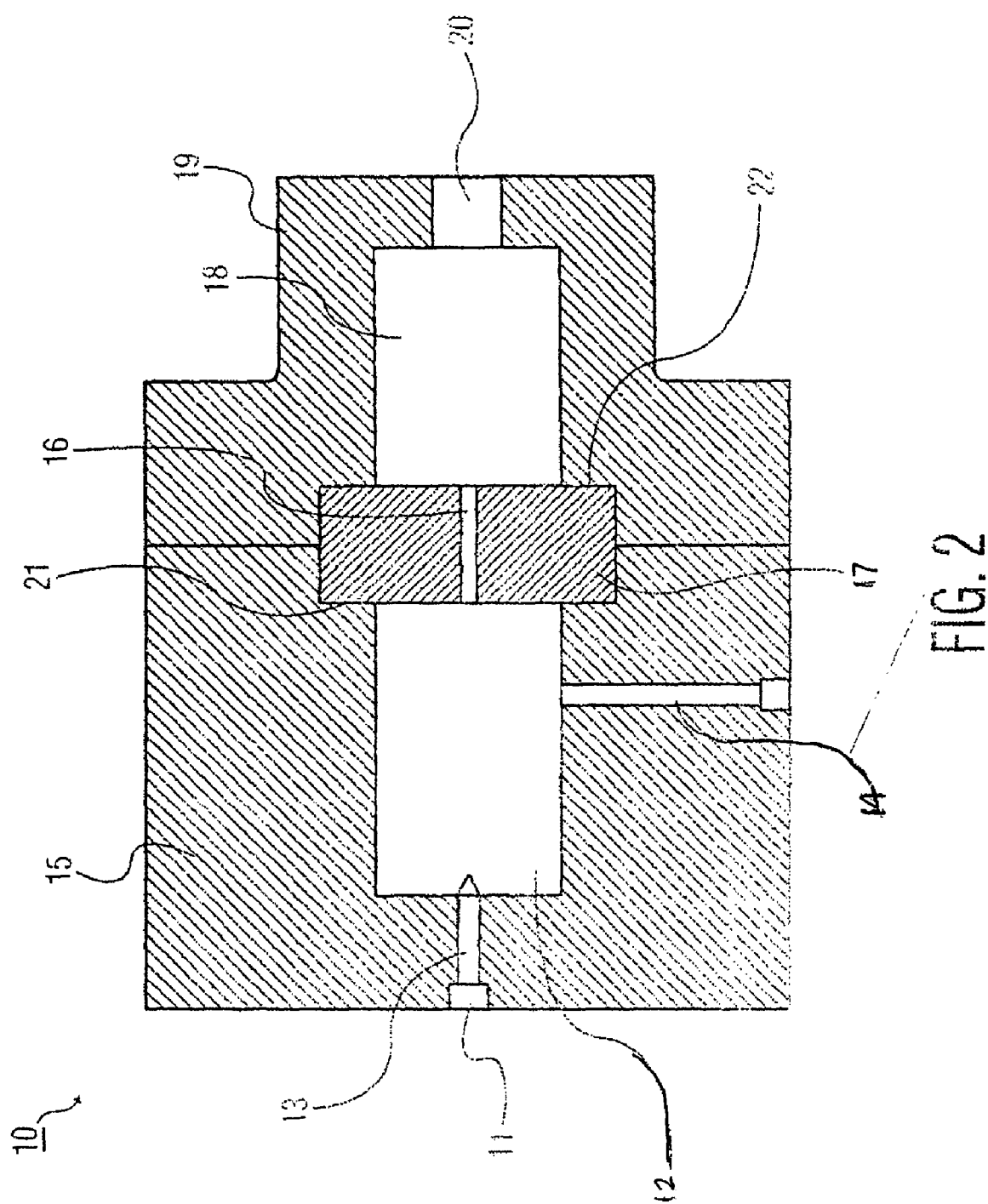
FIG. 2 is a cross-sectional view of the apparatus showing the mixing zone, the cavitation zone, and the expansion zone.
Figure 3:
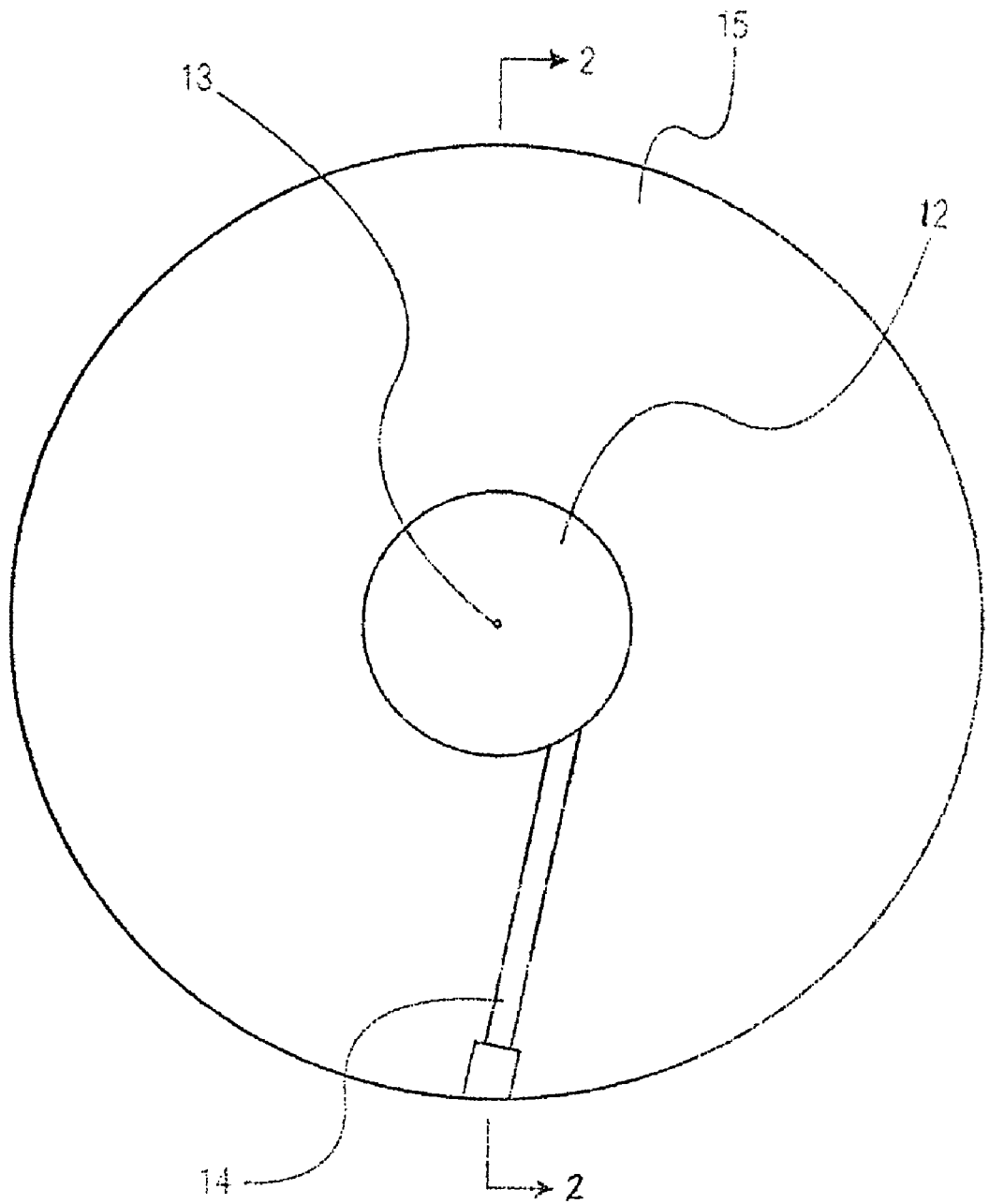
FIG. 3 is a cross-sectional view of the mixing zone showing the conduits which introduce the heavy oil and solvent to the mixing chamber.

Referring now to the drawings, an apparatus 10 for treating or destructuring a heavy oil in accordance with the present invention includes a cylindrical mixing chamber 12, a nozzle or capillary 16 in which cavitation occurs, and an expansion chamber 18. The mixing chamber 12 is surrounded by metal jacketing 15, the nozzle or capillary 16 is surrounded by metal jacketing 17, and the expansion chamber 18 is surrounded by metal jacketing 19.

Metal jacketing 15 includes a recess 21, and metal jacketing 19 includes a recess 22. Recess 21 and recess 22 surround or enclose metal jacketing 17 surrounding nozzle or capillary 16. Metal jacketing 15 and metal jacketing 19 are fastened to each other with fastening means such as bolts, screws, or dowels (not shown), thereby enclosing metal jacketing 17 in recesses 21 and 22, and ensuring that the nozzle or capillary 16 is disposed between mixing chamber 12 and expansion chamber 18.

Preheated heavy oil enters mixing chamber 12 through conduit 11, which terminates in a conical atomization nozzle 13, whereby the heavy oil enters the mixing chamber 12 in the form of droplets. The preheated organic material, such as an organic solvent, enters the mixing zone 12 through conduit 14.

The preheated organic solvent enters mixing chamber 12 from conduit 14 such that it moves along the cylindrical wall of mixing chamber 12 in a circular or vortexing motion. The droplets of heavy oil, which entered mixing chamber 12 through atomization nozzle 13, contact the organic solvent along the cylindrical wall of the mixing chamber 12, whereby the resulting mixture of heavy oil and organic solvent is passed through mixing chamber 12 as a vortexed mixture of heavy oil and solvent, and into nozzle or capillary 16. As noted hereinabove, the mixture of heavy oil and solvent is passed through nozzle or capillary 16 at a velocity of from about 100 m/sec to about 300 m/sec, and is subjected to a pressure drop of from about 150 psig to about 5,000 psig. As the mixture of heavy oil and solvent passes through nozzle or capillary 16, the heavy oil is subjected to hydrodynamic cavitation as hereinabove described.

The mixture of heavy oil and solvent then exits the nozzle or capillary 16 and enters expansion chamber 18, wherein cooling of the heavy oil occurs. The resulting destructured heavy oil then exits the expansion chamber 18 through pipe 20. The destructured heavy oil then is transported to a desired location, and/or subjected to further processing, such as, for example, deasphalting and/or distillation or fractionation.

Figure 4:
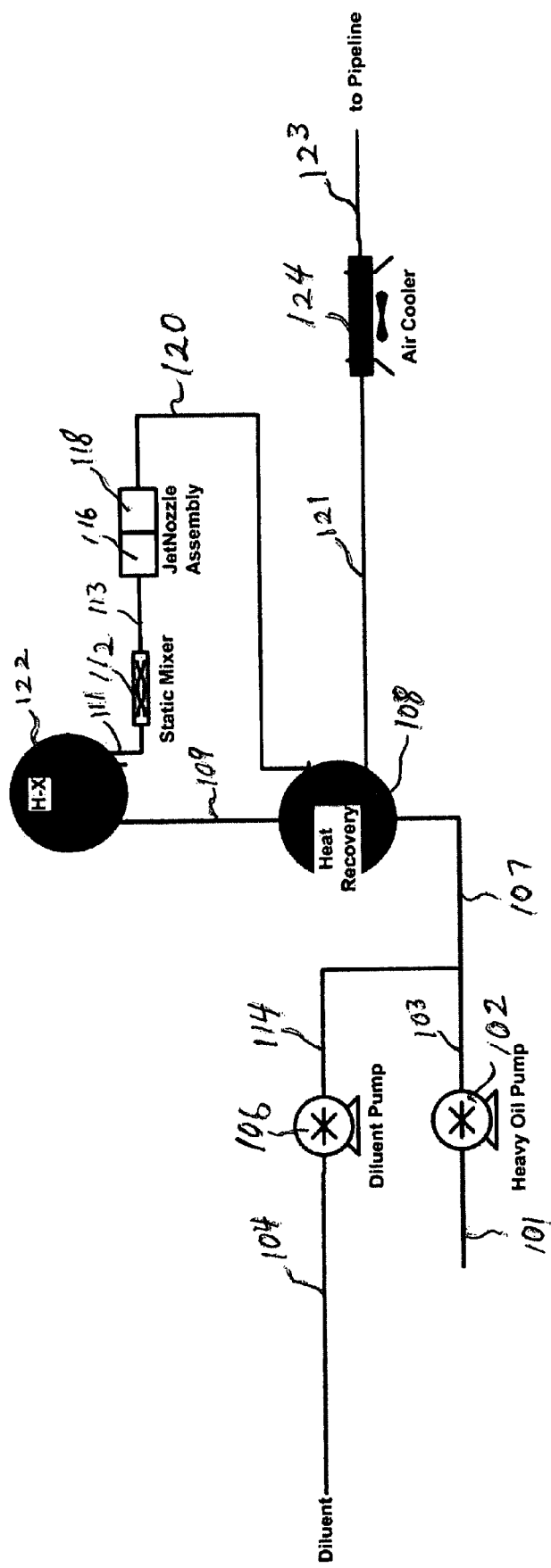
FIG. 4 is a schematic of another embodiment for effecting the destructuring of a heavy oil in accordance with the present invention.

In another embodiment, as shown in FIG. 4, heavy oil in line 101 is passed through pump 102 into line 103. An organic material, such as an organic solvent or diluent, in line 104, is passed through pump 106 into line 114. The organic solvent or diluent in line 114 is mixed with the heavy oil from line 103, and the mixture of heavy oil and organic solvent or diluent is passed through line 107. The mixture of heavy oil and organic solvent or diluent is heated by passing the mixture through heat exchanger 108, whereby the mixture of heavy oil and organic solvent or diluent is heated by passing a heated destructured heavy oil from line 120 through heat exchanger 108, whereby the mixture of untreated heavy oil and organic solvent or diluent is heated and the destructured heavy oil is cooled. The heated mixture of heavy oil and organic solvent or diluent then is passed through line 109 into heat exchanger 122, whereby the mixture of untreated heavy oil and organic solvent or diluent is subjected to further heating. The mixture of heavy oil and organic solvent or diluent is heated by passing a heated gas, such as, for example, a heated mixture of air and natural gas, through heat exchanger 122, whereby the mixture of untreated heavy oil and organic solvent or diluent is subjected to further heating.

The heated mixture of heavy oil and organic solvent or diluent then is passed into line 111, and into static mixer 112. In static mixer 112, the stream of the mixture of heavy oil and organic solvent or diluent is divided, and the divided streams are forced to opposite outside walls, thereby causing a single direction mixing vortex axial to the center line of the static mixer 112. The mixing vortex then is sheared, and division of the stream of heavy oil and organic solvent or diluent reoccurs, with the opposite directional rotation. An example of such a static mixer is a Stratos Tube Mixer, Series 250, sold by Koflo Corporation, of Cary, Ill.

After the heavy oil and organic solvent or diluent are subjected to mixing in static mixer 112, the mixture of heavy oil and organic solvent or diluent is passed through line 113 and into the cavitation zone 116, whereby the mixture of heavy oil and organic solvent or diluent is subjected to cavitation. Cavitation zone 116 includes a cavitation nozzle or capillary (not shown) surrounded by metal jacketing. The mixture of heavy oil and organic solvent or diluent is passed through the nozzle or capillary of the cavitation zone 116 at a velocity of from about 100 m/sec to about 300 m/sec, and is subjected to a pressure drop of from about 150 psig to about 5,000 psig. As the mixture of heavy oil and solvent or diluent passes through the nozzle or capillary of the cavitation zone 116, the heavy oil is subjected to hydrodynamic cavitation.

The mixture of heavy oil and organic solvent or diluent then exits the cavitation zone 116 and enters expansion chamber 118, wherein cooling of the heavy oil occurs. The resulting destructured heavy oil then exits expansion chamber 118 through pipe 120. The destructured heavy oil then enters heat exchanger 108, whereby heat is transferred from the destructured heavy oil to the mixture of untreated heavy oil and solvent or diluent entering heat exchanger 108 from line 107. The cooled destructured heavy oil exits heat exchanger 108 through line 121, and enters air cooler 124, whereby the destructured heavy oil is subjected to further cooling. The heavy oil exits air cooler 124 through line 123, and is subjected to further processing, such as, for example, deasphalting and/or distillation or fractionation.

EXAMPLES

The invention now will be described with respect to the following examples; however, the scope of the present invention is not intended to be limited thereby.

Example 1

A Lloydminster heavy oil, having an API gravity of 12.0°, a specific gravity of 0.986 (density of 0.986 g/cm$^3$), and a kinematic viscosity of 34,805 cSt at 15° C., of 2,795 cSt at 40° C., and of 636 cSt at 60° C., was heated to 400° C. and pumped through a pipe having a diameter of ¼ inch and then through a conical atomization nozzle having a diameter at the tip of 0.03 inch into a mixing chamber having a length of 3 inches and a diameter of 1.5 inches. Pentane solvent was heated to a temperature of 400° C. and pumped through a pipe having a diameter of 0.203 inch into the mixing chamber in an amount of 9 vol. % of the volume of the heavy oil. The heavy oil and pentane were mixed in the mixing chamber for 10 seconds. The mixture of heavy oil and pentane then was passed from the mixing chamber through a cavitation nozzle. The velocity in the nozzle was about 118 m/sec. The cavitation nozzle had a length of 1 inch and a diameter of 0.008 inch. The differential pressure, or pressure drop, across the nozzle was about 410 psig. The mixture of heavy oil and pentane then entered an expansion chamber having a length of 2.25 inches and a diameter of 1.5 inches.

The resulting treated oil had an API gravity of 18.1°, a specific gravity of 0.945 (density of 0.945 g/cm$^3$), a kinematic viscosity of 710 cSt at 15° C., of 183 cSt at 40° C., and of 67 cSt at 60° C.

Example 2

The Lloydminster heavy oil of Example 1 was treated under the conditions described in Example 1 except that the heavy oil was heated to 380° C., pentane was added to the heavy oil in an amount of 15 vol. % of the volume of heavy oil, and the mixture of heavy oil and pentane was passed through the cavitation nozzle at a velocity in the nozzle of about 120 m/sec and a pressure drop of about 450 psig.

The resulting treated oil had an API gravity of 20.6°, a specific gravity of 0.930 (density of 0.930 g/cm$^3$), and a kinematic viscosity of 610 cSt at 15° C., of 104 cSt at 40° C., and of 44 cSt at 60° C.

Example 3

The Lloydminster heavy oil of Example 1 was treated under the conditions described in Example 1 except that each of the heavy oil and pentane were heated to 350° C., and the mixture of heavy oil and pentane was passed through the cavitation nozzle at a velocity in the nozzle of about 168 m/sec, and subjected to a pressure drop of about 1,100 psig.

The resulting treated oil had an API gravity of 21.2°, a specific gravity of 0.927 (density of 0.927 g/cm$^3$), and a kinematic viscosity of 109 cSt at 15° C., of 35 cSt at 40° C., and of 12 cSt at 60° C.

Example 4

A bitumen from the cold lake region of Alberta, having an API gravity of 10.0°, a specific gravity of 0.996 (density of 0.996 g/cm$^3$), and a dynamic viscosity of 138,000 cP at 15° C. was heated to 380° C. and pumped through a pipe having a diameter of ¼ inch. Pentane solvent was heated to a temperature of 400° C., and pumped through a pipe having a diameter of ¼ inch. The pentane solvent then was mixed with the bitumen in a pipe having a diameter of ¼ inch, in an amount of 17 vol % of the volume of the bitumen. The mixture of bitumen and pentane then was mixed further in a static mixer (Stratos Tube Mixer, 250 Series, Koflo Corporation, Cary, Ill.) having a length of 9 inches and a diameter of ¼ inch. The bitumen and pentane were mixed in the static mixer for 10 seconds. The mixture of bitumen and pentane then was passed from the mixing chamber through a cavitation nozzle. The velocity in the nozzle was 203 m/sec. The cavitation nozzle had a length of 0.56 inch and a diameter of 0.007 inch. The differential pressure, or pressure drop, across the nozzle was about 2,400 psig. The mixture of bitumen and pentane then entered an expansion chamber having a length of 2.25 inches and a diameter of 1.5 inches.

The resulting treated oil had an API gravity of 20.9°, a specific gravity of 0.928 (density of 0.928 g/cm$^3$), and a dynamic viscosity of 300 cP at 15° C., or kinematic viscosity of 323 cSt at 15° C.

Example 5

A Smiley Coleville heavy oil having an API gravity of 14.2°, a specific gravity of 0.9703 (density of 0.9703 g/cm$^3$), and a dynamic viscosity of 7,600 cP at 15° C. and 7,190 cP at 20° C. was treated under the conditions described in Example 4 hereinabove, except that each of the heavy oil and pentane were heated to 200° C., the pentane was added in amount of 13 vol. % of the volume of the heavy oil, the velocity of the mixture of pentane and heavy oil in the cavitation nozzle was 186 m/sec, and the pressure drop across the cavitation nozzle was 2,000 psig.

The resulting treated oil had an API gravity of 22.5°, a specific gravity of 0.919 (density of 0.919 g/cm³), and a dynamic viscosity of 340 cP at 15° C., which is equivalent to a kinematic viscosity of 370 cSt at 15° C.

The disclosure of all patents and publications, including published patent applications, are hereby incorporated by reference to the same extent as if each patent and publication were specifically and individually incorporated by reference.

It is to be understood, however, that the scope of the present invention is not to be limited to the specific embodiments described above. The invention may be practiced other than as particularly described and still be within the scope of the accompanying claims.

What is claimed is:

1. A process for treating a heavy oil, comprising:
    subjecting a liquid comprising a heavy oil and an organic material which is not a heavy oil, wherein said organic material is a liquid at standard temperature and pressure or a supercritical fluid, to hydrodynamic cavitation to reduce the viscosity of said heavy oil, wherein liquid is present in an amount of at least 40 vol. % of the mixture of heavy oil and organic material.

2. The process of claim 1 wherein, prior to mixing of said heavy oil with said organic material, said heavy oil is heated to a temperature of from about 75° C. to about 450° C., and said organic material is heated to a temperature of from about 75° C. to about 800° C.

3. The process of claim 1 wherein said organic material is present in said mixture of said heavy oil and said organic material in an amount of from about 5 vol. % to about 25 vol. % of the volume of said heavy oil.

4. The process of claim 1 wherein said mixture of said heavy oil and said organic material is subjected to a velocity of from about 100 msec to about 300 m/sec, a pressure drop of from about 150 psi to about 5,000 psi, and hydrodynamic cavitation to reduce the viscosity of said heavy oil.

5. The process of claim 4 wherein said mixture of said heavy oil and said organic material is subjected to a velocity of from about 150 m/sec to about 300 m/sec.

6. The process of claim 5 wherein said mixture of said heavy oil and said organic material is subjected to a velocity of from about 200 m/sec to about 300 m/sec.

7. The process of claim 4 wherein said mixture of said heavy oil and said organic material is subjected to a pressure drop of from about 400 psig to about 4,000 psig.

8. The process of claim 7 wherein said mixture of said heavy oil and said organic material is subjected to a pressure drop of from about 400 psig to about 2,000 psig.

9. The process of claim 8 wherein said mixture of said heavy oil and said organic material is subjected to a pressure drop of from about 400 psig to about 1,500 psig.

10. The process of claim 9 wherein said mixture of said heavy oil and said organic material is subjected to a pressure drop of from about 1,000 psig to about 1,500 psig.

11. The process of claim 2 wherein said heavy oil is heated to a temperature of from about 150° C. to about 450° C.

12. The process of claim 11 wherein said heavy oil is heated to a temperature of from about 200° C. to about 450° C.

13. The process of claim 12 wherein said heavy oil is heated to a temperature of from about 200° C. to about 400° C.

14. The process of claim 13 wherein said heavy oil is heated to a temperature of from about 300° C. to about 400° C.

15. The process of claim 2 wherein said organic material is heated to a temperature of from about 150° C. to about 800° C.

16. The process of claim 15 wherein said organic material is heated to a temperature of from about 300° C. to about 800° C.

17. The process of claim 16 wherein said organic material is heated to a temperature of from about 300° C. to about 600° C.

18. The process of claim 17 wherein said organic material is heated to a temperature of from about 300° C. to about 400° C.

19. The process of claim 1 wherein said heavy oil and said organic material are mixed in a first zone and said mixture of said heavy oil and said organic material is subjected to hydrodynamic cavitation in a second zone.

20. The process of claim 1 wherein said heavy oil is treated in the absence of hydrogen.

21. The process of claim 1 wherein said organic material is selected from the group consisting of pentane, liquefied petroleum gases, alcohols, ethers, and mixtures thereof.

22. The process of claim 21 wherein said organic material is pentane.

23. The process of claim 1 wherein said organic material has been subjected to a temperature above the critical temperature and a pressure above the critical pressure, whereby the organic material is a supercritical fluid.

24. The process of claim 19 wherein the width of said second zone is less than the width of said first zone.

25. The process of claim 24 wherein the ratio of the width of said second zone to the width of said first zone is from about 1/230 to about 1/75.

26. The process of claim 19 wherein the ratio of the length of the cavitation zone to the width of the cavitation zone is from about 10 to about 125.

27. The process of claim 26 wherein the ratio of the length of the cavitation zone to the width of the cavitation zone is from about 50 to about 125.

28. The process of claim 1 wherein liquid is present in an amount of at least 60 vol. % of the total volume of the mixture of heavy oil and organic material.

29. A process treating a heavy oil comprising:
    mixing a heavy oil and an organic material other than a heavy oil in a mixing zone, wherein said organic material is a supercritical fluid, to provide a mixture of said heavy oil and said organic material, and wherein liquid is present in an amount of at least 40 vol. % of the mixture of said heavy oil and said organic material; and
    subjecting said mixture to hydrodynamic cavitation in a cavitation zone, wherein the ratio of the width of said cavitation zone to the width of said mixing zone is from about 1/230 to about 1/75, and wherein the ratio of the length of said cavitation zone to the width of said cavitation zone is from about 10 to about 125.

30. A process for treating a heavy oil, comprising:
    passing a feed which consists essentially of a liquid at standard temperature and pressure, wherein said liquid comprises a heavy oil and an organic material which is not a heavy oil, through a hydrodynamic cavitation zone, wherein a portion of the liquid which is passed through said cavitation zone is formed into microbubbles dispersed in said liquid, whereby said liquid is subjected to hydrodynamic cavitation to reduce the viscosity of said heavy oil.

31. The process of claim 30 wherein said organic material is selected from the group consisting of pentane, liquefied petroleum gases, alcohols, ethers, and mixtures thereof.

32. The process of claim 31 wherein said organic material is pentane.

33. The process of claim 30 wherein said heavy oil and an organic material are mixed in a mixing zone, to provide a mixture of said heavy oil and said organic material, and said mixture of said heavy oil and said organic material is subjected to said hydrodynamic cavitation in said cavitation zone.

34. The process of claim 33 wherein the width of said hydrodynamic cavitation zone is less than the width of said mixing zone.

35. The process of claim 34 wherein the ratio of the width of said hydrodynamic cavitation zone to the width of said mixing zone is from about 1/230 to about 1/75.

36. The process of claim 33 wherein, prior to mixing said heavy oil with said organic material, said heavy oil is heated to a temperature of from about 75° C. to about 450° C., and said organic material is heated to a temperature of from about 75° C. to about 800° C.

37. The process of claim 36 wherein said heavy oil is heated to a temperature of from about 150° C. to about 450° C.

38. The process of claim 37 wherein said heavy oil is heated to a temperature of from about 200° C. to about 450° C.

39. The process of claim 38 wherein said heavy oil is heated to a temperature of from about 200° C. to about 400° C.

40. The process of claim 39 wherein said heavy oil is heated to a temperature of from about 300° C. to about 400° C.

41. The process of claim 36 wherein said organic material is heated to a temperature of from about 150° C. to about 800° C.

42. The process of claim 41 where said organic material is heated to a temperature of from about 300° C. to about 800° C.

43. The process of claim 42 wherein said organic material is heated to a temperature of from about 300° C. to about 600° C.

44. The process of claim 43 wherein said organic material is heated to a temperature of from about 300° C. to about 400° C.

45. The process of claim 30 wherein said organic material is present in said liquid in an amount of from about 5 vol. % to about 25 vol. % of the volume of said heavy oil.

46. The process of claim 30 wherein said liquid is passed through said cavitation zone at a velocity of from about 100 m/sec to about 300 m/sec, and is subjected to a pressure drop of from about 150 psi to about 5,000 psi.

47. The process of claim 46 wherein said liquid is passed through said cavitation zone at a velocity of from about 150 m/sec to about 300 m/sec.

48. The process of claim 47 wherein said liquid is passed through said cavitation zone at a velocity of from about 200 m/sec to about 300 m/sec.

49. The process of claim 46 wherein said liquid is subjected to a pressure drop of from about 400 psig to about 4,000 psig.

50. The process of claim 49 wherein said liquid is subjected to a pressure drop of from about 400 psig to about 2,000 psig.

51. The process of claim 50 wherein said liquid is subjected to a pressure drop of from about 400 psig to about 1,500 psig.

52. The process of claim 51 wherein said liquid is subjected to a pressure drop of from about 1,000 psig to about 1,500 psig.

53. The process of claim 30 wherein the ratio of the length of the cavitation zone to the width of the cavitation zone is from about 10 to about 125.

54. The process of claim 53 wherein the ratio of the length of the cavitation zone to the width of the cavitation zone is from about 50 to about 125.

55. A process for treating a heavy oil, comprising:
mixing a heavy oil, and an organic material other than a heavy oil in a mixing zone, wherein each of said heavy oil and said organic material is a liquid at standard temperature and pressure, to provide a feed which consists essentially of a liquid at standard temperature and pressure;
passing said feed through a hydrodynamic cavitation zone, wherein the ratio of the width of said cavitation zone to the width of said mixing zone is from about 1/230 to about 1/75, and ratio of the length of said caviation zone to the width of said cavitation zone is from about 10 to about 125, wherein a portion of the liquid which is passed through said cavitation zone is formed into microbubbles dispersed in said liquid, whereby said liquid is subjected to hydrodynamic cavitation to reduce the viscosity of said heavy oil.

* * * * *